United States Patent

Wu et al.

[11] Patent Number: 5,876,331
[45] Date of Patent: Mar. 2, 1999

[54] ENDOSCOPE WITH IMPROVED FLEXIBLE INSERTION TUBE

[75] Inventors: Su-Syin Wu, Irvine; Nancy S. Chu, Laguna Niguel, both of Calif.

[73] Assignee: Johnson & Johnson Medical, Inc., Arlington, Tex.

[21] Appl. No.: 747,689

[22] Filed: Nov. 12, 1996

[51] Int. Cl.$^6$ .................................................. A61B 1/00
[52] U.S. Cl. ..................... 600/139; 600/140; 600/133; 138/118; 138/140
[58] Field of Search ................................ 600/139, 140, 600/141, 142, 143, 144, 133; 138/118, 140, 145, 148, 149, 137, 138, 139

[56] References Cited

U.S. PATENT DOCUMENTS 4,753,222  6/1988  Morishita ................................ 600/140
5,217,002  6/1993  Katsurada et al. ....................... 600/139
5,394,864  3/1995  Kobayashi et al. .................. 600/133 X

*Primary Examiner*—Beverly M. Flanagan
*Attorney, Agent, or Firm*—Andrew C. Farmer

[57] ABSTRACT

In a flexible endoscope having a flexible insertion tube comprising a tubular, biocompatible elastomeric outer covering thereabout which encloses an interior space, the improvement according to the present invention comprises a vapor barrier between the outer covering and the interior space. Thus, vapor, such as hydrogen peroxide or other sterilants, passing through the outer covering from an atmosphere thereabout is prevented from entering the interior space by the vapor barrier. Further, the vapor is thus prevented from interacting with substances, such as lubricants, within the interior space to produce agents harmful to the elastomeric covering.

15 Claims, 2 Drawing Sheets

ENDOSCOPE WITH IMPROVED FLEXIBLE INSERTION TUBE

BACKGROUND

1. Field of the Invention

The present invention relates generally to flexible endoscopes; specifically to an improvement in the design of their flexible insertion tubes.

2. State of the Prior Art

A typical endoscope comprises an elongated tube suitable for introduction into a human or animal body. A lens at a distal tip of the endoscope forms an image of an internal area of the body. Means such as fiber optic cables or video transmission transmit the image along the length of the endoscope to a point outside of the body where it can be viewed by a surgeon or other user of the endoscope. Of course, endoscopes are not limited to medical uses, and are also useful in machine diagnostics and repair among other uses. Regardless of its intended use, a flexible distal portion allows the endoscope to negotiate non-linear passages.

In addition to the image transmission means, the distal portion of the endoscope typically contains one or more tubular passages for passing air, liquid, or instruments. Flexible endoscopes usually also contain one or more wires for controlling movement of the tip of the endoscope. A flexible sheath surrounds the flexible portion of the endoscope to protect it from its environment and to protect a patient's body or other environment from the internal parts of the endoscope.

To prevent noscomical infection, endoscopes are typically washed and then either sterilized or subjected to high level disinfection after each use. For added convenience during these procedures, many endoscopes are provided with an entirely water tight structure to protect the internal components of the endoscope from washing, disinfection and sterilization agents. In a flexible endoscope, the flexible elastomeric sheath surrounding the flexible portion of the endoscope forms an integral part of this water tight structure.

Delicate medical instruments, such as flexible endoscopes and the like, are notoriously difficult to sterilize and disinfect due to the complexity of their structure and design. Elastomeric parts on flexible endoscopes cannot survive the intense heat of steam sterilization typically used in the hospital and clinical environment. Typically, these instruments are now dipped into baths of liquid sterilants or high level disinfectants, with some of the liquid being forced through the long lumens within the endoscopes. Such processes have limitations. For instance, the high toxicity of many of the preferred liquid sterilants or disinfectants classifies them as hazardous waste after the procedure and makes them dangerous to work with. Also, liquid does not penetrate small crevices within an instrument as well as gaseous phase sterilants such as high pressure steam and gaseous chemical sterilants.

Gaseous sterilization with strong oxidizing agents such as hydrogen peroxide is a well established method for sterilizing delicate instruments such as flexible endoscopes. Ethylene oxide (EtO) gas is one such sterilant. However, it must be handled carefully as it is extremely toxic and mutagenic. One particularly effective gaseous technology is hydrogen peroxide gas plasma sterilization such as that provided by the STERRAD® Systems of Advanced Sterilization Products, a division of Johnson & Johnson Medical, Inc. In this type of system, instruments are placed into a sealed chamber and exposed to an atmosphere containing hydrogen peroxide in the gaseous phase. The chamber is placed under a vacuum prior to admitting the hydrogen peroxide to encourage the hydrogen peroxide vapor to reach all areas of the instrument. Once the vapor has reached all surfaces on the instruments in the chamber, an electromagnetic field is applied to the chamber driving the hydrogen peroxide into the plasma phase of matter. This enhances the sterilizing effect of the hydrogen peroxide. Further, when the field is released, the free radicals in the plasma recombine to form water and oxygen, thereby leaving no harmful residuals.

However, when flexible endoscopes have been subjected to this type of process, many experienced rapid degradation of their elastomeric outer sheath. This was curious as it was not thought that the hydrogen peroxide would affect such parts. Even more perplexing was the apparent random nature of the problem. Many theories were propounded, including some unknown interaction between the hydrogen peroxide, the plasma state and the elastomers. It was discovered that the degradation stems not from the action of the oxidizer on the elastomer, but from the action of the oxidizer on lubricating substances within the interior space within the insertion tube which in turn form compounds which degrade the elastomers. Certain lubricants found in endoscopes and other instruments breakdown in the oxidizing environment of the hydrogen peroxide vapor to form acids which can damage the elastomeric parts of delicate medical instruments. The lubricants are members of the class of metal dichalcogenides, such as molybdenum disulfide.

The oxidative chemical sterilant vapor reaches interior space primarily through two avenues. First, vapor may enter the space through a pressure relief port in the insertion tube. A significant area of unused space occupies the interior of the insertion tube of most flexible endoscopes. Of course, this space is filled with gas, typically air. As the pressure is reduced during a sterilization procedure, the gas trapped inside of the endoscope exerts tremendous pressure against the elastomeric sheath. If this pressure is not released, the sheath could rupture. Many endoscopes are provided with a sealable port leading into the interior of the endoscope. During sterilization in a reduced pressure environment the port may be opened to allow the interior of the endoscope to communicate with the sterilization atmosphere and thus relieve the excess pressure within the endoscope. The port is also used to check for leaks in the endoscope, especially in the sheath, through the controlled application of gas pressure to the endoscope's interior while it is submerged in water. Co-pending U.S. patent application Ser. No. 08/446,377, and its foreign equivalents including EPO Application No. 96303585.2, incorporated herein by reference, disclose a two-way check valve and filter mechanism to relieve the pressure differential across the outer sheath without admitting hydrogen peroxide or other gaseous sterilants into the inner space of the insertion tube.

Second, polyurethane is a preferred elastomer for forming the outer sheath due to its biocompatibility, surface lubricity softness and to the ease with which it can be manufactured. However, oxidative sterilant vapors such as hydrogen peroxide can permeate through a sheath formed of polyurethane to enter the interior space of the endoscope. Once within the interior space it interacts with lubricants such as molybdenum disulfide to form acidic products which attack the polyurethane sheath. This action also degrades the effectiveness of the lubricant, but the sheath generally fails before the lubricant is exhausted in this manner. Further, the chemical sterilant vapor may cause other damage within the insertion tube and it may not dissipate during the normal course of the sterilization cycle, leaving residual chemical sterilant within the interior space after the sterilization procedure is completed, thus extending the chemical reaction between sterilants gas and molybdenum disulfide.

U.S. Pat. No. 4,753,222, incorporated herein by reference, discloses an endoscope sheath with a two layer construction. However, it does not disclose that the inner layer may be made to prevent passage of hydrogen peroxide or other sterilants into the interior space of the insertion tube.

SUMMARY OF THE INVENTION

The present invention overcomes these limitations and others in the prior art by providing a vapor barrier between the outer sheath and the interior space of the insertion tube, thereby preventing hydrogen peroxide or other sterilants from entering the insertion tube interior space and interacting with the lubricants and mechanisms therein.

In a flexible endoscope having a flexible insertion tube comprising a tubular, biocompatible elastomeric outer covering thereabout which encloses an interior space, the improvement according to the present invention comprises a vapor barrier between the outer covering and the interior space. Thus, vapor passing through the outer covering from an atmosphere thereabout is prevented from entering the interior space by the vapor barrier. Further, the vapor is thus prevented from interacting with substances within the interior space to produce agents harmful to the elastomeric covering.

Preferably, the vapor barrier is formed of a material impervious to the vapor phase of sterilizing substances such as hydrogen peroxide, ethylene dioxide, chlorine, and chlorine dioxide. Suitable materials include, polyolefins, fluorinated polyolefins, polyvinyldene chloride, polyvinyldene fluoride, fluro-chloro polymers or non-porous polymer coating materials such as Paralyne, a product of Union Carbide. The elastomeric outer covering is preferably formed of polyurethane.

The vapor barrier may be formed in any number of ways, but it is preferably formed either by coating a polymer onto an inner surface of the elastomeric outer covering, or by co-extruding the material of the vapor barrier with the outer covering.

A method according to the present invention for protecting a biocompatible elastomeric coating on a flexible endoscope insertion tube from the effects of exposing the insertion tube to a sterilizing chemical vapor, the method comprises the following steps. An interior space of the insertion tube is enclosed with a tubular, biocompatible elastomeric outer covering. A vapor barrier is placed between the outer covering and the interior space, thereby preventing any of the chemical vapor which passes through the outer covering from entering the interior space. The chemical vapor is thus prevented from interacting with substances within the interior space to produce agents harmful to the elastomeric covering.

DETAILED DESCRIPTION

Figure 1:
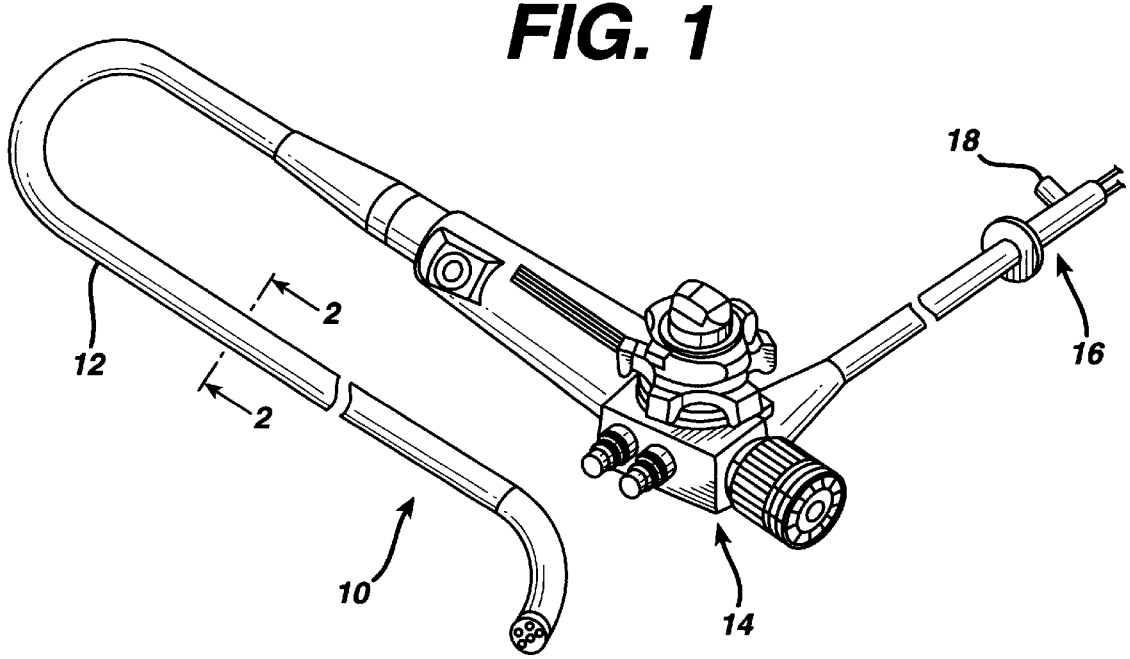
FIG. 1 is a perspective view of a flexible endoscope according to the present invention.
Figure 2:
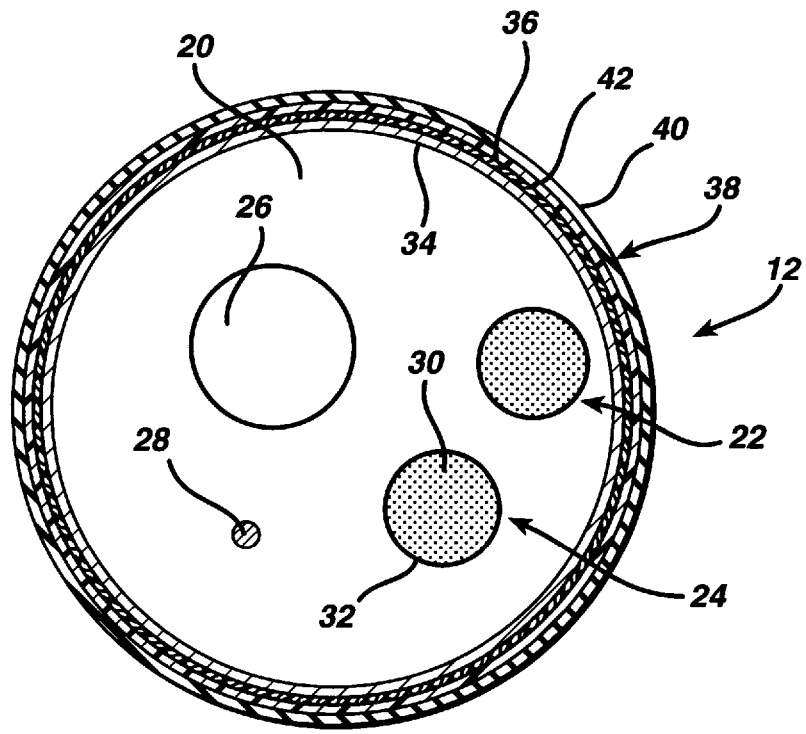
FIG. 2 is a sectional view of an insertion portion of the endoscope taken along line 2—2 of FIG. 1.

FIGS. 1 and 2 depict an endoscope 10 according to the present invention which comprises in gross, a flexible insertion tube 12, a handpiece 14 and an accessory connector 16 with a valved port 18 leading to an interior space 20 of the insertion tube 12. The port 18 thus allows pressure communication between the interior space 20 and atmosphere.

As best seen in FIG. 2, the interior space 20 carries a pair of fiber optic bundles 22 and 24, one for carrying light for illumination and the other for carrying the image to be viewed. Some other type of flexible endoscopes use a CCD chip (charge couple device) for electronic image transmission. A lumen 26 and a steering mechanism 28 also pass through the interior space 20. Each fiber optic bundle 22 and 24 comprises a large number of individual optical fibers 30 and a sheath 32 surrounding the fibers 30. Generally, the sheath 32 is formed of silicone. Molybdenum disulfide lubricates the fiber optic bundles 22 and 24 to reduce friction between the individual optical fibers 30 as they slide against each other during the maneuvering of the insertion tube 12. Molybdenum disulfide is generally also dispersed throughout the interior space 20 of the insertion tube 12 to also lubricate the steering mechanism 28, the lumen 26 and any other components as they slide against each other. Other flexible endoscope, such as gastrointestinal scopes and colonoscopes, may have more internal channels to facilitate passage of air, water and the like.

Figure 3:
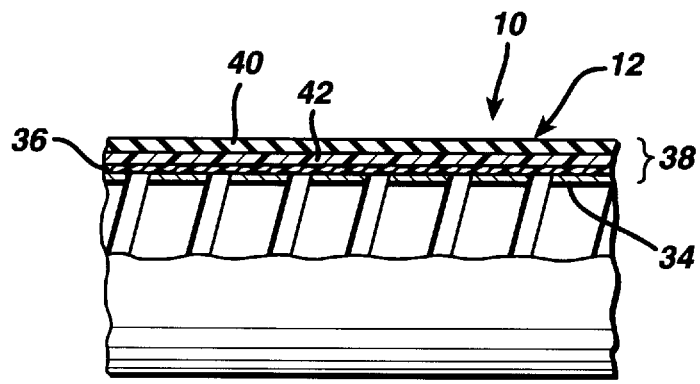
FIG. 3 is a partial sectional view of the insertion portion of FIG. 2, showing the construction of the sheath.

Turning to FIG. 3, the insertion tube 12 comprises a metal inner spiral layer 34 for rigidity, over which lies a braided metal layer 36 and an outer sheath 38. The sheath comprises two layers; an outer layer 40 which ultimately contacts the body of the patient and an inner vapor barrier layer 42. Since the insertion tube 12 is inserted inside the body, the material choice is critical. The material of the outer layer 40 must be flexible and biocompatible. Polyurethanes are commonly used for such application. They offer a good combination of lubricity, flexibility, strength, durability, and stability, as well as biocompatibility. However, due to the vapor permeability of polyurethane, in a typical endoscope with a single layer sheath formed of polyurethane, vastly greater amounts of hydrogen peroxide or other sterilant may, in some instances, enter the interior of the interior space by diffusion through the sheath than would enter through the pressure equalization port.

In the present endoscope 10, the inner vapor barrier layer 42 prevents the sterilant from passing into the interior space 20. It may be formed of any substance which will be flexible, not interact with, absorb or allow permeation of vapor based sterilants such as hydrogen peroxide, chlorine dioxide, ethylene dioxide and the like. Preferred materials include polyolefins, fluorinated polyolefins, polyvinyldene chloride, polyvinyldene fluoride, or fluro-chloro polymers. The inner layer 42 may be formed by any known method, however, it is preferred to either co-extrude the inner layer 42 with the outer layer 40 or to deposit the inner layer 42 onto the outer layer 40 as a film coating. In the latter instance a non-porous polymer such as Paralyne (a product of Union Carbide) may be employed or, a separate internal layer between the multilayer sheath (38, 36 & 34) and the inner channels (including metal braiding) made of the above mentioned polymers, and the internal components of the endoscopes can be installed.

In addition to hydrogen peroxide gas plasma, there are other sterilization methods which employ oxidization processes or strong oxidizers for sterilization. Some other oxidizing sterilants and methods include ozone ($O_3$), chlorine dioxide ($ClO_2$), EtO, hydrogen peroxide vapor without plasma, and peracetic acid. These oxidizing sterilants are expected to react similarly with molybdenum disulfide and cause material degradation. The two-layer construction of the sheath 38 will protect the endoscope 10 against attack by any of these agents.

In a sterilization procedure, the endoscope 10 will typically be washed to free it of organic matter and then placed into a sealed chamber (not shown). The pressure in the chamber will be reduced and then a vapor based sterilizing agent such as hydrogen peroxide will be introduced into the chamber. The sterilant may penetrate and sterilize the outer layer 40, but the inner layer 42 will block its passage into the interior space 20. At the time the sterilant is introduced, the port 18 will be closed thereby preventing access to the interior space 20 through this avenue. As the interior space 20 is otherwise sealed, there remains no avenue for the sterilant to pass into the interior space and interact with the mechanisms or lubricants therein. If using a plasma type process, a plasma is then created which enhances the sterilization process and leaves behind no harmful residuals.

While the invention has been particularly described in connection with specific embodiments thereof, it is to be understood that this is by way of illustration and not of limitation, and that the scope of the appended claims should be construed as broadly as the prior art will permit. For instance, a particular construction of an endoscope 10 and insertion tube 12 have been illustrated. However, the invention is not limited thereto; there are many variations of such designs known to those of skill in the art, and one of ordinary skill in the art would understand that the present teaching of the two-layer sheath 38 could be applied to any common design of endoscope and insertion tube. The endoscope 10 illustrated herein is suitable for a sigmoidoscopy, however, it will be appreciated that other types of endoscopes are capable of incorporating the present invention. Also, polymer materials are disclosed as preferred for the inner layer 42, but other materials such as metals, ceramics and others which can meet the requirements set forth herein may be substituted therefor. While the invention is most useful in vapor phase sterilization, the construction disclosed herein would also prevent liquids which may penetrate a polyurethane outer sheath from entering the interior space.

What is claimed is:

1. In a flexible endoscope having a flexible insertion tube comprising a tubular, biocompatible elastomeric outer covering thereabout which encloses an interior space, the improvement wherein the outer covering is vapor transmissive of oxidative sterilant vapors and wherein the insertion tube further comprises a vapor barrier, which is impermeable by and non-absorptive of oxidative sterilant vapors, between the outer covering and the interior space whereby vapor passing through the outer covering from an atmosphere thereabout is prevented from entering the interior space by the vapor barrier, and further whereby the vapor is thus prevented from interacting with substances within the interior space to produce agents harmful to the elastomeric covering.

2. A flexible endoscope according to claim 1 wherein the vapor barrier is formed of a material impervious to the vapor phase of sterilizing substances selected from the group consisting of hydrogen peroxide, ethylene dioxide, chlorine, and chlorine dioxide.

3. A flexible endoscope according to claim 2 wherein the elastomeric outer covering is formed of polyurethane.

4. A flexible endoscope according to claim 1 wherein the vapor barrier is formed of a material impervious to vapor phase hydrogen peroxide.

5. A flexible endoscope according to claim 4 wherein the elastomeric outer covering is formed of polyurethane.

6. A flexible endoscope according to claim 4 wherein the vapor barrier comprises a material selected from the group consisting of polyolefins, fluorinated polyolefins, polyvinyldene chloride, polyvinyldene fluoride, and fluro-chloro polymers.

7. A flexible endoscope according to claim 4 wherein the vapor barrier comprises a tubular film.

8. A flexible endoscope according to claim 7 wherein the film comprises a polymer coating on an inner surface of the elastomeric outer covering.

9. A flexible endoscope according to claim 7 wherein the film comprises a polymer co-extruded with the outer covering.

10. A method for protecting a biocompatible elastomeric coating on a flexible endoscope insertion tube from the effects of exposing the insertion tube to a sterilizing chemical vapor, the method comprising the steps of:

enclosing an interior space of the insertion tube with a tubular, biocompatible elastomeric outer covering which is permeable to the sterilizing chemical vapor;

exposing the insertion tube to the sterilizing chemical vapor; and placing a vapor barrier which is impermeable to and non-absorptive of the sterilizing chemical vapor between the outer covering and the interior space, thereby preventing any of the chemical vapor which passes through the outer covering from entering the interior space, whereby the chemical vapor is thus prevented from interacting with substances within the interior space to produce agents harmful to the elastomeric covering.

11. The method according to claim 10 wherein the elastomeric outer covering is formed of polyurethane.

12. The method according to claim 11 wherein the vapor barrier comprises a material selected from the group consisting of polyolefins, fluorinated polyolefins, polyvinyldene chloride, polyvinyldene fluoride, and fluoro-chloro polymers.

13. The method according to claim 11 wherein the vapor barrier is formed as a tubular film.

14. The method according to claim 13 and further comprising the step of coating a polymer onto an inner surface of the elastomeric outer covering to form the film.

15. The method according to claim 13 and further comprising the step of co-extruding a polymer with the outer covering to form the film.

* * * * *